(12) United States Patent
Ajiki

(10) Patent No.: US 9,555,261 B2
(45) Date of Patent: Jan. 31, 2017

(54) PHOTOTHERAPEUTIC DEVICE AND PHOTOTHERAPEUTIC METHOD

(71) Applicant: Panasonic Intellectual Property Management Co., Ltd., Osaka (JP)

(72) Inventor: Kaori Ajiki, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 135 days.

(21) Appl. No.: 14/563,045

(22) Filed: Dec. 8, 2014

(65) Prior Publication Data

US 2015/0182758 A1   Jul. 2, 2015

(30) Foreign Application Priority Data

Dec. 27, 2013   (JP) ................................. 2013-272326

(51) Int. Cl.
*A61N 5/06* (2006.01)
*A61B 18/00* (2006.01)

(52) U.S. Cl.
CPC ... *A61N 5/0616* (2013.01); *A61B 2018/00791* (2013.01); *A61B 2018/00863* (2013.01); *A61N 2005/0626* (2013.01); *A61N 2005/0647* (2013.01); *A61N 2005/0652* (2013.01); *A61N 2005/0659* (2013.01); *A61N 2005/0663* (2013.01)

(58) Field of Classification Search
CPC .......... A61B 2018/00791; A61B 2018/00863; A61N 2005/0626; A61N 2005/0647; A61N 5/0616

USPC ...................... 606/2–3, 9–13; 607/80, 88–95
See application file for complete search history.

(56) References Cited

U.S. PATENT DOCUMENTS

| | | | |
|---|---|---|---|
| 6,596,016 B1* | 7/2003 | Vreman | A61N 5/0621 128/903 |
| 2005/0177093 A1 | 8/2005 | Barry et al. | |
| 2007/0129776 A1* | 6/2007 | Robins | A61N 5/0613 607/88 |
| 2007/0257256 A1 | 11/2007 | Kugler | |

(Continued)

FOREIGN PATENT DOCUMENTS

| | | |
|---|---|---|
| JP | 2005-027702 | 2/2005 |
| JP | 2007-300112 | 11/2007 |

(Continued)

OTHER PUBLICATIONS

The Extended European Search Report dated Mar. 31, 2015 for European Patent Application No. 14195822.3.

(Continued)

*Primary Examiner* — Gary Jackson
*Assistant Examiner* — Jonathan Kuo
(74) *Attorney, Agent, or Firm* — Greenblum & Bernstein, P.L.C.

(57) ABSTRACT

A phototherapeutic device includes a sheet member that is attachable to a skin; a skin-condition sensor that is disposed in the sheet member and that detects information related to a condition of the skin; and a light-emitting device unit that is disposed in the sheet member, the light-emitting device unit operating on the basis of the information detected by the skin-condition sensor. The light-emitting device unit includes a plurality of light-emitting devices that emit light having different wavelengths.

9 Claims, 8 Drawing Sheets

(56) References Cited

U.S. PATENT DOCUMENTS

| | | | | |
|---|---|---|---|---|
| 2008/0269849 | A1* | 10/2008 | Lewis | A61N 5/0613 607/91 |
| 2009/0058274 | A1 | 3/2009 | Yokoyama et al. | |
| 2010/0305484 | A1 | 12/2010 | Grollier et al. | |
| 2011/0257712 | A1* | 10/2011 | Wells | A61B 5/6821 607/90 |
| 2013/0066404 | A1 | 3/2013 | Tapper et al. | |
| 2015/0127072 | A1* | 5/2015 | Pomar | A61N 5/0616 607/90 |

FOREIGN PATENT DOCUMENTS

| | | |
|---|---|---|
| JP | 2009-048837 | 3/2009 |
| JP | 2011-041706 | 3/2011 |
| JP | 2011-505897 | 3/2011 |
| JP | 2013-154229 | 8/2013 |
| JP | 2013-168575 | 8/2013 |
| KR | 10-0963687 | 6/2010 |
| WO | 20111037122 | 3/2011 |
| WO | 2012/011042 | 1/2012 |
| WO | 20131151128 | 10/2013 |

OTHER PUBLICATIONS

Takanori Kiyokura et al., "Wearable Laser Blood Flowmeter" NTT Technical Review, pp. 24-27, Nov. 2005.

Satoshi Aihara et al., "Trend in Research on Organic Imaging Devices" NHK Science & Technology Research Laboratories R&D No. 132, pp. 4-11, Mar. 2012.

* cited by examiner

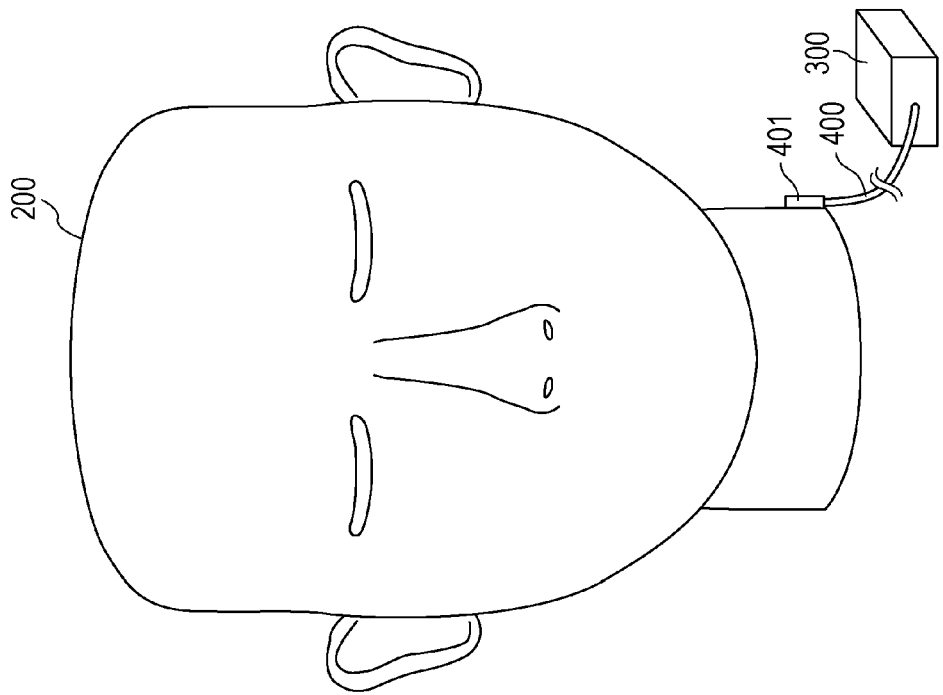
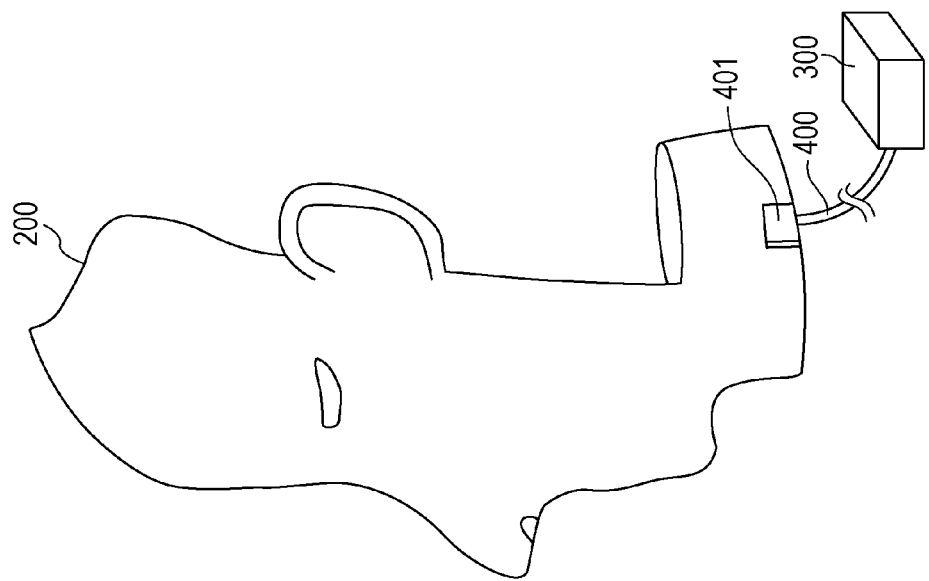

| BLOCK 551 | SKIN-CONDITION SENSOR 552 | LIGHT-EMITTING DEVICE UNIT 553 | THRESHOLD 554 |
|---|---|---|---|
| FIRST BLOCK | 1ST TO 3RD SKIN-CONDITION SENSOR | 1ST TO 6TH LIGHT-EMITTING DEVICE UNIT | $Th_1$ |
| SECOND BLOCK | 4TH TO 6TH SKIN-CONDITION SENSOR | 7TH TO 12TH LIGHT-EMITTING DEVICE UNIT | $Th_2$ |
| .... | .... | .... | .... |
| LTH BLOCK | ... TO MTH SKIN-CONDITION SENSOR | ... TO NTH LIGHT-EMITTING DEVICE UNIT | $Th_L$ |

PHOTOTHERAPEUTIC DEVICE AND PHOTOTHERAPEUTIC METHOD

CROSS REFERENCE TO RELATED APPLICATION

The present application claims the benefit of Japanese Patent Application No. 2013-272326 filed on Dec. 27, 2013. The entire disclosure of the above-identified application, including the specification, drawings and claims, is incorporated herein by reference in its entirety.

BACKGROUND

1. Technical Field

The present disclosure relates to a phototherapeutic device and a phototherapeutic method.

2. Description of the Related Art

To date, a cosmetic device (see Japanese Unexamined Patent Application Publication No. 2013-154229) that irradiates the skin with light guided from a lens or an optical facial beautifying mask (see Japanese Unexamined Patent Application Publication No. 2005-27702) including a light source unit that irradiates the face with light having different hues through a mask have been disclosed.

SUMMARY

However, the above-described configurations have difficulty in effectively rejuvenating the skin.

One non-limiting and exemplary embodiment provides a phototherapeutic device that can more effectively rejuvenate the skin.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

In one general aspect, the techniques disclosed here feature a phototherapeutic device that includes a sheet member that is attachable to a skin; a skin-condition sensor that is disposed in the sheet member and that detects information related to a condition of the skin; and a light-emitting device unit that is disposed in the sheet member, the light-emitting device unit operating on the basis of the information detected by the skin-condition sensor, wherein the light-emitting device unit includes a plurality of light-emitting devices that emit light having different wavelengths.

Note that general and specific aspects of the present disclosure may be implemented in a form of a method.

A phototherapeutic device disclosed herein can more effectively rejuvenate the skin.

BRIEF DESCRIPTION OF THE DRAWINGS

FIGS. 2A and 2B illustrate an example of an appearance of a phototherapeutic device according to a second embodiment of the disclosure.

FIG. 7 illustrates an example of contents in a control rule table according to the second embodiment.

DETAILED DESCRIPTION

Underlying Knowledge

Figure 1:
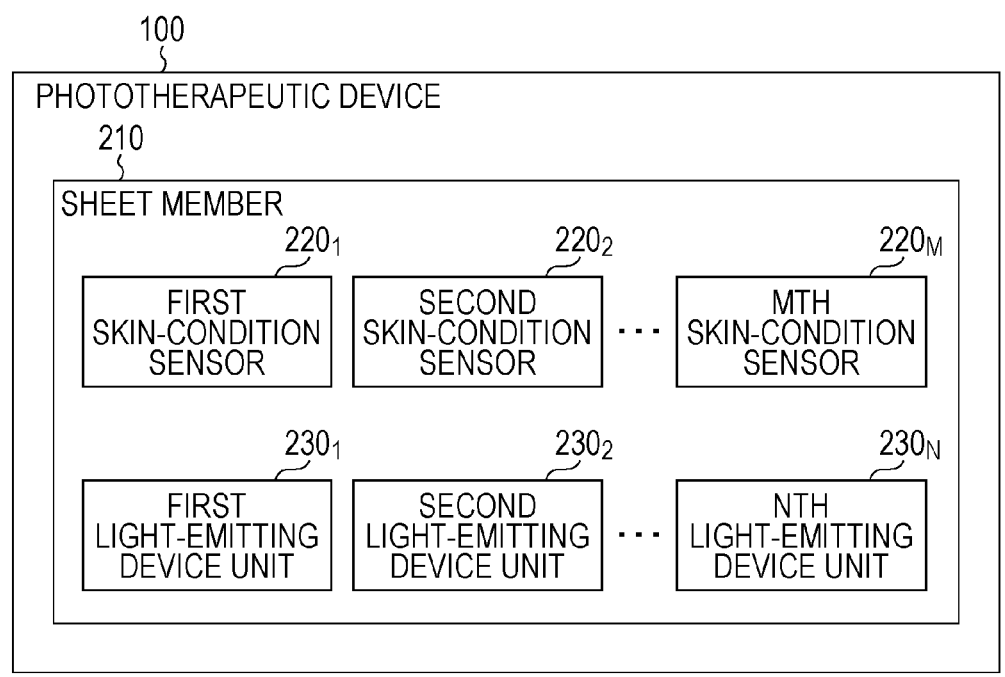
FIG. 1 illustrates an example of the configuration of a phototherapeutic device according to a first embodiment of the disclosure.

Cosmetic devices used to rejuvenate the skin by irradiating the skin with light (hereinafter referred to as "phototherapeutic devices") have been developed (see, for example, Japanese Unexamined Patent Application Publication Nos. 2013-154229 and 2005-27702). Here, rejuvenation of the skin is a concept including, for example, improvement of blood circulation, activation of fibroblast, improvement of lymphatic circulation, whitening, suppression of occurrence of active oxygen, expansion of capillaries, acceleration of metabolism, enhancement of tissue regeneration capability, and muscle relaxant.

A phototherapeutic device described in Japanese Unexamined Patent Application Publication No. 2013-154229 has a light emission port, through which light is emitted, at an end of a hand-held cylindrical body. A phototherapeutic device described in Japanese Unexamined Patent Application Publication No. 2005-27702 includes a large number of light emitting diodes (LEDs) disposed on a face sheet that covers the entire face.

The user applies the light emission port of the phototherapeutic device according to Japanese Unexamined Patent Application Publication No. 2013-154229 to a portion of the skin that the user desires to rejuvenate. Instead, the user covers the entirety of his/her face with the face sheet described in Japanese Unexamined Patent Application Publication No. 2005-27702. Thus, the technologies of Japanese Unexamined Patent Application Publication Nos. 2013-154229 and 2005-27702 (hereinafter referred to as "existing technologies") can rejuvenate the skin and improve the skin conditions.

The intensity of light (irradiance and irradiation time) with which the phototherapeutic device irradiates the skin differs depending on the conditions of the skin including the thickness of discoloration, the degree of darkening, or the degree of activation of fibroblast. For example, a portion having thicker discoloration requires an irradiation with intenser light. On the other hand, an excessive irradiation of a portion of the skin that has fully been rejuvenated with light is not desirable. Thus, desirably, each portion of the skin is irradiated with light having an appropriate intensity that is neither too low nor too high.

The skin conditions, however, are usually uneven and thus appropriately irradiating the entirety of the skin with light is difficult. Moreover, even in the case where each portion is individually irradiated with light, appropriately determining which portion of the skin is to be irradiated with light of how much intensity or for how long is difficult. In other words, existing technologies have difficulty in effectively rejuvenating the skin.

To address this situation, a phototherapeutic device of the disclosure includes a sheet member that is attachable to a skin; a skin-condition sensor that is disposed in the sheet member and that detects information related to a condition of the skin; and a light-emitting device unit that is disposed in the sheet member, the light-emitting device unit operating on the basis of information detected by the skin-condition sensor. The light-emitting device unit includes a plurality of light-emitting devices that emit light having different wavelengths.

Thus, the phototherapeutic device of the disclosure can more effectively rejuvenate the skin.

Referring now to the drawings, embodiments of the disclosure are described in detail below.

First Embodiment

A first embodiment of the disclosure is an example of a basic form of the disclosure.

FIG. 1 illustrates an example of the configuration of a phototherapeutic device 100 according to this embodiment.

In FIG. 1, the phototherapeutic device 100 includes a sheet member 210, first to Mth skin-condition sensors $220_1$ to $220_M$, and first to Nth light-emitting device units $230_1$ to $230_N$.

The sheet member 210 is a member that can be attached to the skin.

The first to Mth skin-condition sensors $220_1$ to $220_M$ are disposed in the sheet member 210 at different positions of the sheet member 210. Each of the first to Mth skin-condition sensors $220_1$ to $220_M$ detects the conditions of a portion of the skin adjacent to the skin-condition sensor.

The first to Nth light-emitting device units $230_1$ to $230_N$ are disposed at positions on the sheet member 210 corresponding to the positions of the respective first to Mth skin-condition sensors $220_1$ to $220_M$. The first to Nth light-emitting device units $230_1$ to $230_N$ operate in accordance with information related to the condition detected by the corresponding skin-condition sensors.

Each of the light-emitting device units $230_1$ to $230_N$ includes multiple light-emitting devices that emit light having different wavelengths.

Each of the light-emitting device units $230_1$ to $230_N$ may reduce or stop light emission when the degree to which the information detected by the corresponding skin-condition sensor has changed after the start of light emission has arrived at a predetermined threshold.

Since the phototherapeutic device 100 can irradiate each portion of the skin with light appropriate for the conditions of the portion, the skin can be effectively rejuvenated.

The phototherapeutic device 100 may have only one skin-condition sensor on the sheet member 210 instead of multiple skin-condition sensors. The phototherapeutic device 100 may have only one light-emitting device unit on the sheet member 210 instead of multiple light-emitting device units.

Second Embodiment

A second embodiment of the disclosure is an example of a specific form when the disclosure is applied to a face sheet that covers the entire face.

Appearance and Configuration of Phototherapeutic Device

Firstly, the appearance and the configuration of a phototherapeutic device 100 according to the embodiment will be described.

Appearance of Phototherapeutic Device

FIGS. 2A and 2B illustrate an example of the appearance of the phototherapeutic device 100 according to the embodiment. FIG. 2A illustrates the appearance of the phototherapeutic device 100 when viewed from the side. FIG. 2B illustrates the appearance of the phototherapeutic device 100 when viewed from the front.

As illustrated in FIGS. 2A and 2B, the phototherapeutic device 100 includes a sheet device 200 and a control unit 300.

The sheet device 200 is a device having a three-dimensional shape that covers the face, both ears, the submandibular portion (these portions are collectively called the "face", as appropriate below) and the surface of the neck. The base material of the sheet device 200 is a sheet member having elasticity and flexibility. Examples usable as the base material include a sheet member formed of a cured product of an energy-ray curable composition containing an acryloyl group-terminated urethane polymer and an acrylic monomer (see Japanese Unexamined Patent Application Publication No. 2013-168575).

The sheet device 200 has slits shaped so as to correspond to the shape of the closed eyes and openings shaped so as to correspond to the nostrils. Specifically, compared to typical face sheets, the sheet device 200 has a characteristic shape that covers the neck portion in addition to the upper eyelid, the lower eyelid, the lips, the ears, and the submandibular portion.

When placed at a predetermined portion of the face, the sheet device 200 can keep closely adhering to the skin surface of the entire face with the effect of the surface tension. For securing sufficient adherence, a biocompatible adhesive such as spirit gum, a silicone adhesive, or a latex adhesive may additionally be used. It is desirable that the sheet device 200 can be selected from among multiple sizes in accordance with various sizes of the face.

On the surface of the sheet member serving as the sheet device 200 on the side on which the sheet member closely adheres to the face, multiple skin-condition sensors and multiple light-emitting device units (see FIG. 3) are disposed. The configuration of the sheet device 200 on which the multiple skin-condition sensors and the multiple light-emitting device units are arranged will be described in detail below.

The control unit 300 is a unit protected by a housing made of a material such as plastics. The control unit 300 is connected to the sheet device 200 using a cable 400. Specifically, the control unit 300 is connected to each of the first to Mth skin-condition sensors $220_1$ to $220_M$ of the sheet device 200. The control unit 300 is connected to each of the first to Nth light-emitting device units $230_1$ to $230_N$ of the sheet device 200. It is desirable that the cable 400 have such a length that the control unit 300 can be held in a pocket of the user's cloth.

It is desirable that the sheet device 200 and the control unit 300 be attachable to and detachable from each other using a connector 401 and the cable 400. This configuration enables replacement of the sheet device 200 with a new sheet device every time the user uses it.

Configuration of Sheet Device

Figure 3:
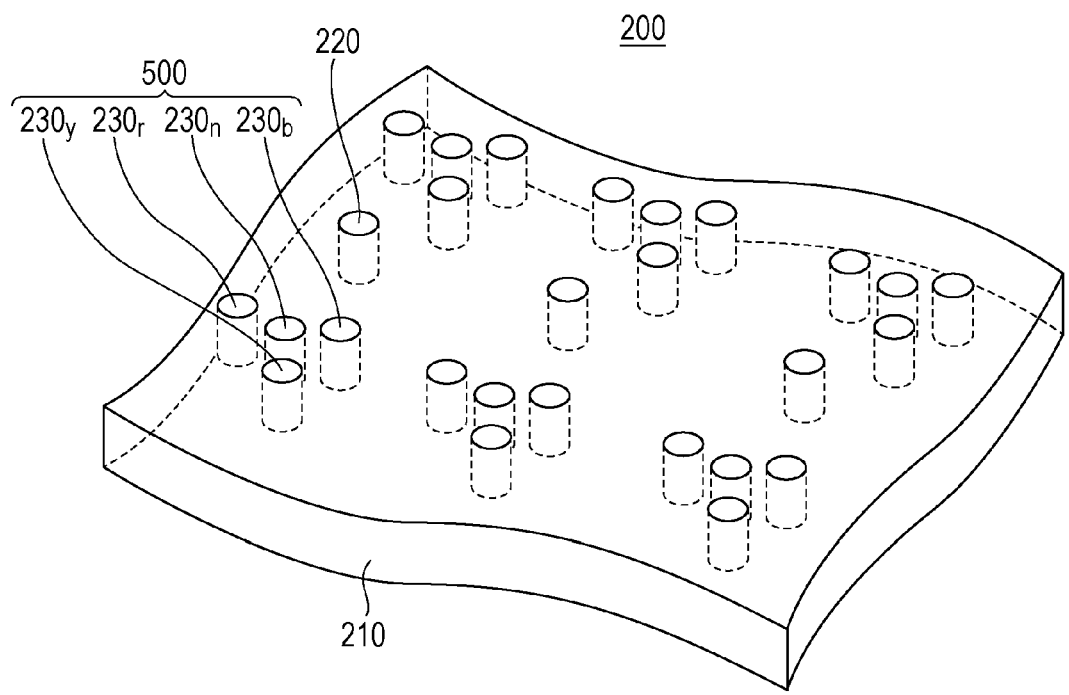
FIG. 3 illustrates an example of the configuration of a sheet device according to the second embodiment.

FIG. 3 illustrates an example of the configuration of the sheet device 200. FIG. 3 illustrates a portion of the entire sheet device 200.

In FIG. 3, the sheet device 200 has a configuration in which the skin-condition sensors 220 and light-emitting device units 500 are embedded in the sheet member 210.

Each skin-condition sensor 220 detects the condition of a portion of the skin adjacent to the skin-condition sensor. In this embodiment, each skin-condition sensor 220 is a blood flow sensor that measures the blood flow in the skin capillaries of the skin at the adjacent portion. A blood-flow detection surface of each skin-condition sensor 220 is exposed from the surface of the sheet member 210 that comes into contact with the skin.

Each light-emitting device unit 500 includes multiple light-emitting devices that emit light having different wavelengths. In this embodiment, each light-emitting device unit 500 includes a light-emitting device $230_y$, which is a yellow LED, a light-emitting device $230_r$, which is a red LED, a light-emitting device $230_n$, which is a near infrared LED, and a light-emitting device $230_b$, which is a blue LED. Light emission surfaces of the light-emitting devices $230_y$, $230_r$, $230_n$, and $230_b$ are exposed from the surface of the sheet member 210 that comes into contact with the skin.

Each of the multiple skin-condition sensors may correspond to multiple light-emitting device units.

The light-emitting device $230_y$, which is a yellow LED, emits light of the yellow range in which the wavelength ranges from 570 nm to 590 nm. The light-emitting device $230_y$ is configured and disposed so that, for example, the irradiance of approximately 0.1 mW/cm$^2$ is obtained at the surface of the sheet device 200 that closely adheres to the skin.

The light-emitting device $230_r$, which is a red LED, emits light of the red range in which the wavelength ranges from 620 nm to 750 nm. The light-emitting device $230_r$ is configured and disposed so that, for example, the irradiance of approximately 1 mW/cm$^2$ is obtained at the surface of the sheet device 200 that closely adheres to the skin.

The light-emitting device $230_n$, which is a near infrared LED, emits light of the near infrared range in which the wavelength ranges from 800 nm to 1000 nm. The light-emitting device 230, is configured and disposed so that, for example, the irradiance of approximately 1 mW/cm$^2$ is obtained at the surface of the sheet device 200 that closely adheres to the skin.

The light-emitting device $230_b$, which is a blue LED, emits light of the blue range in which the wavelength ranges from 440 nm to 490 nm. The light-emitting device $230_b$ is configured and disposed so that, for example, the irradiance of approximately 1 mW/cm$^2$ is obtained at the surface of the sheet device 200 that closely adheres to the skin.

Various researches have reported the relationship between the color (wavelength range) and the irradiance of light emitted by a light-emitting device and the effect on the skin (for example, see Japanese Unexamined Patent Application Publication No. 2011-41706).

Irradiation of the skin with light of the yellow range enhances the lymphatic circulation and whitening. Thus, light emission of the light-emitting device $230_y$, which is a yellow LED, has effects of reduction of discoloration and darkening and shrinkage of the pores.

Irradiation of the skin with light of the red range enhances the blood circulation, collagen formation, and activation of fibroblast. Thus, light emission of the light-emitting device $230_r$, which is a red LED, has an effect of reduction of wrinkles or slackening.

Irradiation of the skin with light of the near infrared range has effects of expansion of capillaries, improvement of blood circulation, acceleration of metabolism, enhancement of tissue regeneration capability, muscle relaxation, and enhancement of collagen formation. Thus, light emission of the light-emitting device $230_n$, which is a near infrared LED, has effects of lessening nasolabial folds, lifting up the skin, and reducing fine wrinkles.

Irradiation of the skin with light of the blue range has effects of suppression of occurrence of active oxygen and disinfection. Thus, light emission of the light-emitting device $230_b$, which is a blue LED, has an effect of reduction of acne or eczema.

It is desirable that the skin-condition sensors and the light-emitting devices in the disclosure be sized as small as possible.

Examples usable as a small-sized skin-condition sensor include a blood flow sensor described in "Wearable Laser Blood Flowmeter" written by Takanori Kiyokura, Shinji Mino, and Junichi Shimada in NTT Technical Review November 2005, issued by Nippon Telegram and Telephone Corporation (NTT Microsystem Integration Laboratories), pp. 25 to 27. Between a laser diode and a phototransistor included in the blood flow sensor, an organic phototransistor formed by a polymer thin film transistor described in Japanese Unexamined Patent Application Publication No. 2007-300112 is usable as the phototransistor.

In addition, examples usable as a small-sized light-emitting device include an organic LED formed by printing using a polymer described in Japanese Unexamined Patent Application Publication No. 2009-48837.

Configuration of Skin-Condition Sensor

Figure 4:
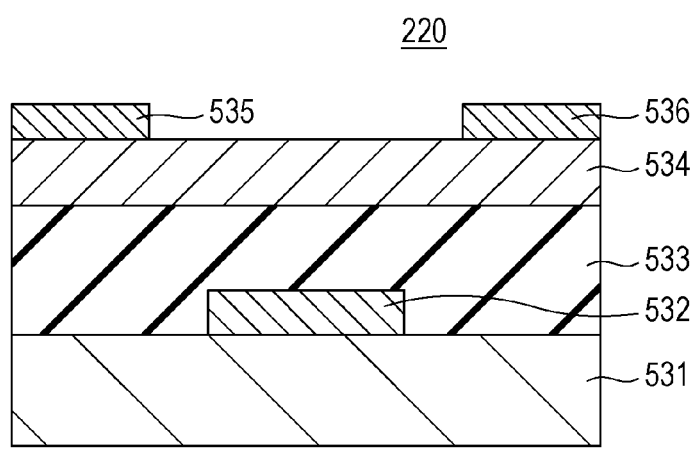
FIG. 4 schematically illustrates an example of the configuration of a skin-condition sensor according to the second embodiment.

FIG. 4 schematically illustrates an example of the configuration of the skin-condition sensor 220 including an organic thin film transistor.

As illustrated in FIG. 4, the skin-condition sensor 220 has a configuration in which a gate insulating layer 533 and an organic molecule layer 534 are stacked on a gate electrode layer 532 disposed on the surface of an elastic base member 531 and in which a source electrode 535 and a drain electrode 536 are disposed on the surface of the organic molecule layer 534 while being spaced apart from each other.

In this embodiment, the sheet device 200 includes M skin-condition sensors $220_1$ to $220_M$. Part of the sheet member 210 may form the elastic base member used for the skin-condition sensor.

Unit by which Sheet Device is Controlled

In this embodiment, the operation of the sheet device 200 is controlled per each section obtained by dividing the sheet device 200 into multiple sections. Hereinbelow, each section of the sheet device 200 or each unit by which the sheet device 200 is controlled is called a "block".

Figure 5:
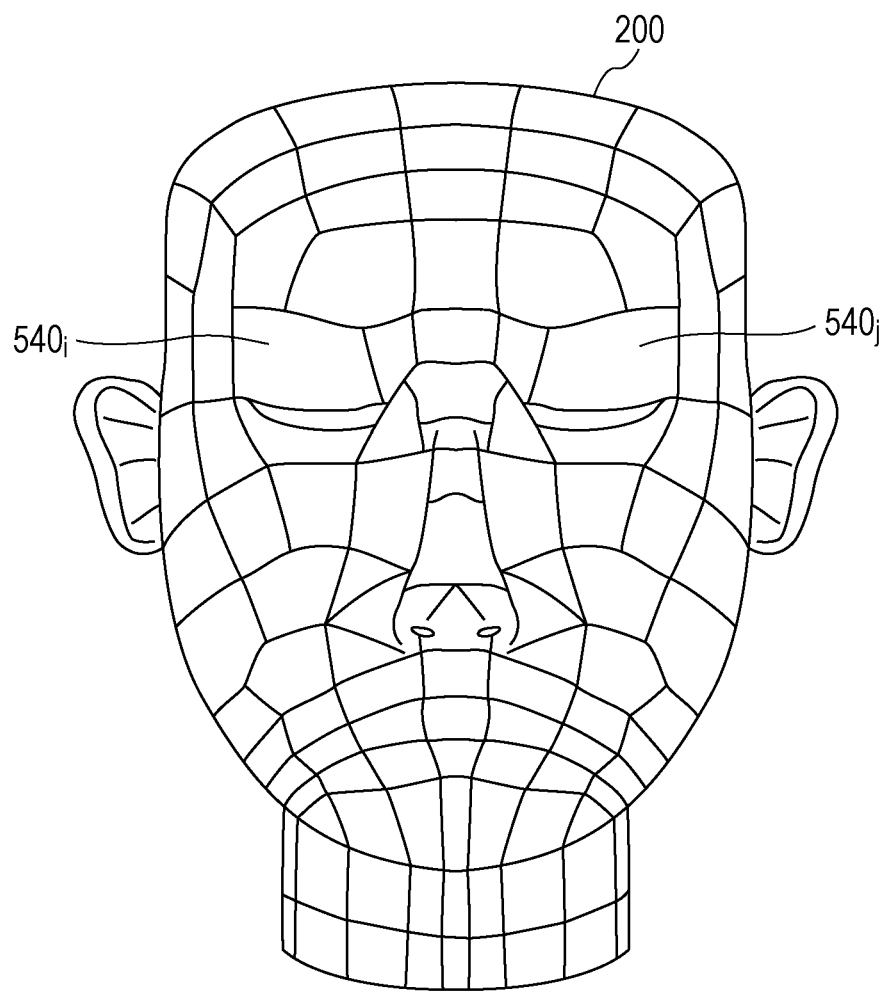
FIG. 5 illustrates an example of an arrangement of blocks according to the second embodiment.

FIG. 5 illustrates an example of an arrangement of blocks in the sheet device 200. FIG. 5 corresponds to FIG. 2A.

As illustrated in FIG. 5, multiple blocks corresponding to small sections of the entire face, for example, L blocks $540_1$ to $540_L$ are defined in the sheet device 200. For example, the blocks include a block corresponding to a center portion of the forehead and a block corresponding to the right upper eyelid. Thus, the sheet device 200 can individually control turning on/off of light or the intensity of light with which the center portion of the forehead and the right upper eyelid are irradiated. The sheet device 200 may also include a block $540_i$ corresponding to a right eyelid and a block $540_j$ corresponding to a left eyelid.

The eyelids are irradiated with light because of the following reasons. The eyelids are more likely to develop wrinkles due to a muscular decline because the skin of the eyelids is thin and blinking causes frequent muscular movement. Moreover, particularly in the case of women, the eyelids are portions on which thick makeup is put and thus likely to be damaged by frictions at the time of cleansing. Thus, the eyelids are more likely to become wrinkled, slackened, and dried. For these reasons, rejuvenation of the skin of the eyelids by irradiation with light is highly significant.

The skin-condition sensors and the light-emitting device units on the sheet device 200 may be arranged at a uniform density throughout the blocks, at different densities between different blocks, or at different densities within each block.

Multiple skin-condition sensors are disposed in each of L blocks. The number of blocks and the arrangement of the blocks are not limited to those in the case illustrated in FIG. 5. Each block may have at least one light-emitting device unit. The type of light-emitting device unit and/or the number of light-emitting device units included in each block may be appropriately determined. The type of light-emitting device unit and/or the number of light-emitting device units included in each block may be different or the same between different blocks.

Functional Configuration of Phototherapeutic Device

Figure 6:
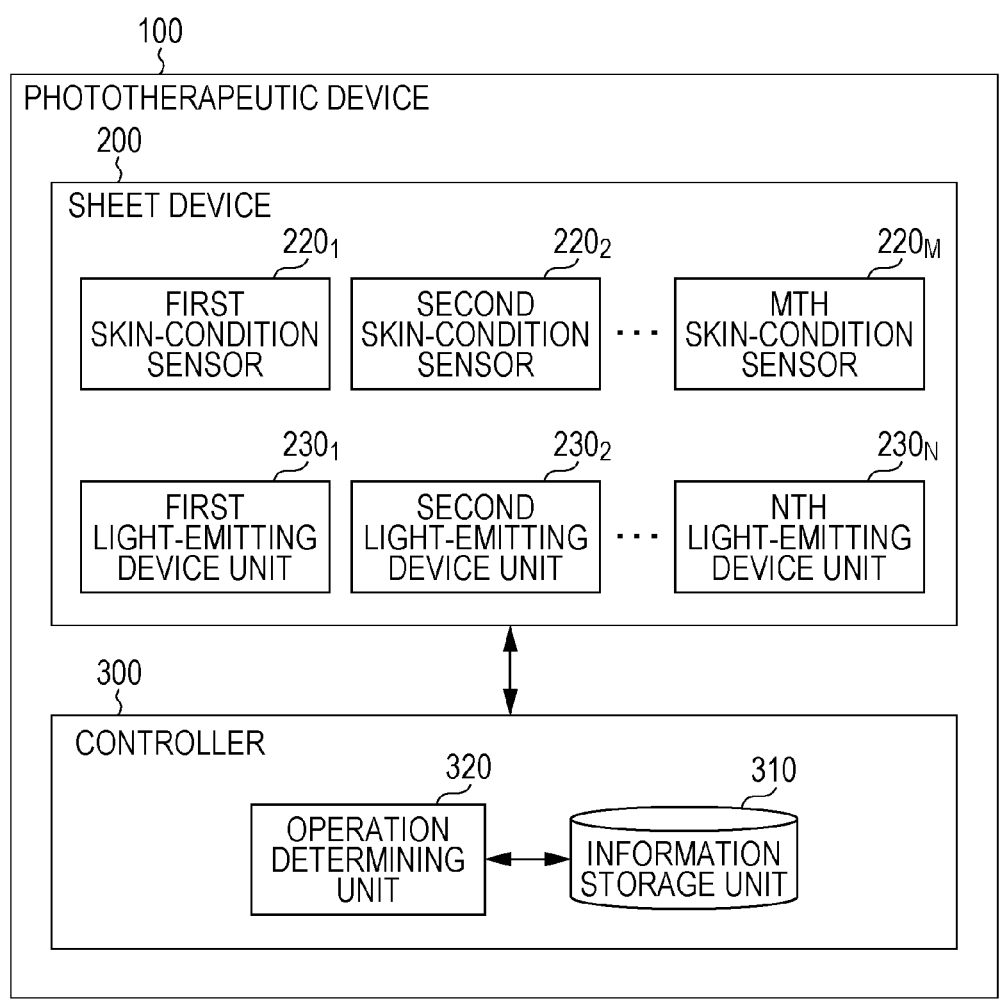
FIG. 6 illustrates an example of the functional configuration of the phototherapeutic device according to the second embodiment.

FIG. 6 illustrates an example of the functional configuration of the phototherapeutic device 100.

In FIG. 6, the phototherapeutic device 100 includes a sheet device 200, which includes first to Mth skin-condition sensors $220_1$ to $220_M$ and first to Nth light-emitting device units $230_1$ to $230_N$, and a control unit 300, which includes an information storage unit 310 and an operation determining unit 320.

In the information storage unit 310, a table that describes which skin-condition sensor and which light-emitting device unit belong to which block (see FIG. 5) and how each block is to be controlled (hereinbelow, the table is called a "control rule table") is stored in advance.

FIG. 7 illustrates examples of the contents of the control rule table.

As illustrated in FIG. 7, the control rule table 550 describes skin-condition-sensor identification information 552 and light-emitting-device-unit identification information 553 for each block in correspondence with block identification information 551. The control rule table 550 also describes a threshold parameter 554 in correspondence with the block identification information 551.

The threshold parameter 554 is a parameter used to determine whether or not light emission should be stopped and represents a value at which the skin is fully rejuvenated by light irradiation and before the light irradiation becomes excessive. For example, the threshold parameter 554 expresses an upper limit of an increase of the blood flow as a result of irradiation of light by a ratio of an increase to an initial blood flow. The threshold parameter 554 may be the same throughout the first to Lth block $540_1$ to $540_L$ or different between different blocks.

The operation determining unit 320 in FIG. 6 is connected to the first to Mth skin-condition sensors $220_1$ to $220_M$ and the first to Nth light-emitting device units $230_1$ to $230_N$ using the cable 400, which connects the control unit 300 and the sheet device 200, and a cable (not illustrated) embedded in the sheet device 200. In other words, the operation determining unit 320 is capable of controlling the operation of the first to Mth skin-condition sensors $220_1$ to $220_M$ by transmitting control signals to the first to Mth skin-condition sensors $220_1$ to $220_M$ and capable of inputting detection values output from the first to Mth skin-condition sensors $220_1$ to $220_M$. The operation determining unit 320 is also capable of controlling the operation of the first to Nth light-emitting device units $230_1$ to $230_N$ by transmitting control signals to the first to Nth light-emitting device units $230_1$ to $230_N$.

The operation determining unit 320 determines the operation of the light-emitting device units disposed in each block of the sheet device 200 on the basis of detection values output from the corresponding skin-condition sensors disposed in the block.

More specifically, the operation determining unit 320 firstly causes specific light-emitting device units to emit light and repeatedly obtains the mean value of detection results output from the corresponding multiple skin-condition sensors in each block (hereinafter the value is referred to as a "block detection value"). Here, if the block includes only one skin detection sensor, calculation of the mean value is not required. Then, the operation determining unit 320 periodically determines whether or not the degree to which the block detection value has changed after the start of light emission arrives at a predetermined threshold. The reason why the mean value is used for determination is to obtain highly reliable data. When the degree to which the block detection value has changed exceeds the predetermined threshold in any of the blocks, the operation determining unit 320 stops or reduces light emission of the light-emitting device units in the block.

The predetermined threshold is determined using the block detection value obtained before the start of light emission and the threshold parameter 554 described in the control rule table 550. The predetermined threshold is effective in preventing the irradiation of light from excessively rejuvenating the skin. Specifically, the operation determining unit 320 controls the operation of each light-emitting device unit so that each block is irradiated with light having an appropriate intensity. The predetermined threshold is described in detail below.

Although not illustrated, the control unit 300 includes, for example, a central processing unit (CPU), a storage medium such as a read only memory (ROM) in which a control program is stored, and an operation memory such as a random access memory (RAM). In this case, the function of each portion of the control unit 300 is implemented by the CPU executing the control program.

Although not illustrated, the control unit 300 includes a power source unit and an operation unit such as a key switch. The power source unit supplies power to operate the CPU and the sheet device 200. The operation unit receives various operations including an operation of starting light emission from a user.

The phototherapeutic device 100 having this configuration is capable of emitting light with an intensity appropriate for each portion of the skin.

Operation of Phototherapeutic Device

Now, the operation of the phototherapeutic device 100 is described.

Figure 8:
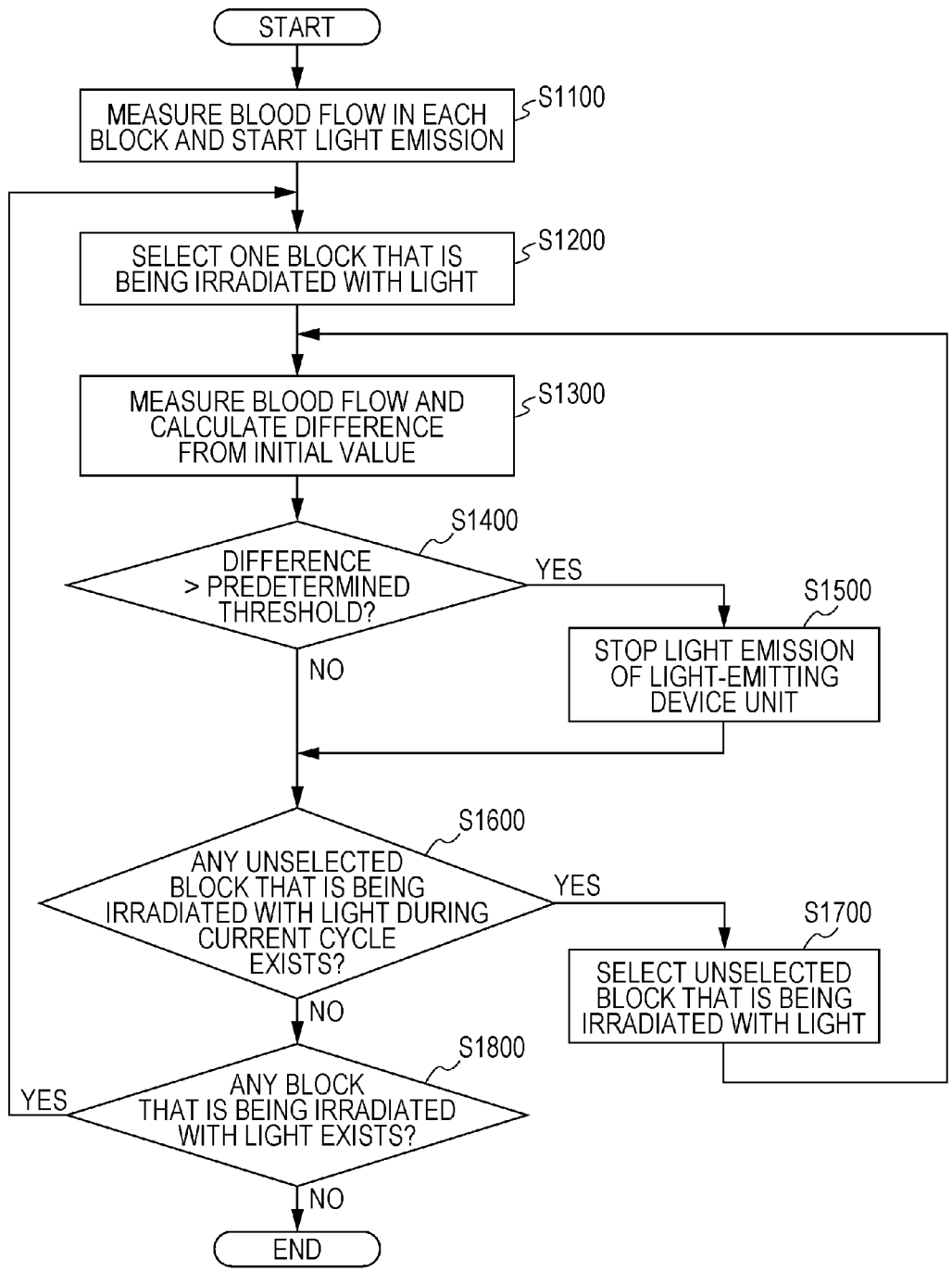
FIG. 8 is a flowchart illustrating an example of the operation of the phototherapeutic device according to the second embodiment.

FIG. 8 is a flowchart illustrating an example of the operation of the phototherapeutic device 100.

The phototherapeutic device 100 starts the following processing when a user instructs the start of the operation in the state where the sheet device 200 is attached to the user's face.

Desirably, the phototherapeutic device 100 allows users to select the wavelength of light that is to be emitted, that is, the effect that the user wants from light irradiation. The description here is given on the assumption that an operation is performed so that light ranging through the yellow range, the red range, the near infrared range, and the blue range is emitted, that is, all the light-emitting devices $230_y$, $230_r$, $230_n$, and $230_b$ (see FIG. 3) of the light-emitting device units 500 are caused to emit light.

In Step S1100, the first to Mth skin-condition sensors $220_1$ to $220_M$ measure the blood flow before light irradiation and output the measured results to the operation determining unit 320. The operation determining unit 320 calculates the block detection value of each block and records the calculated value (hereinafter referred to as an "initial block detection value"). The first to Nth light-emitting device units $230_1$ to $230_N$ start light emission (light irradiation of the skin). Since the blood flow does not start changing immediately after the start of light emission, measurement the blood flow may be started immediately after the start of light emission.

The irradiance and the maximum irradiation time at the start of light emission may be the same or different between the different light-emitting device units. For example, the eyelids have a skin thinner than other portions of the face and eyeballs are located under the eyelids. Thus, desirably, the irradiance of light of the near infrared range or the red range, which particularly has a high capability of penetrating the skin, with which the blocks corresponding to the eyelids are irradiated is reduced compared to that of light with which other blocks are irradiated (for example, 1/10 the irradiance). The irradiance is controlled by controlling, for example, the electric current that the operation determining unit 320 supplies to each light-emitting device unit.

In addition, it is desirable that the maximum irradiation time for the blocks corresponding to the eyelids be reduced compared to that for other blocks or a predetermined threshold for the blocks corresponding to the eyelids be lowered compared to that for other blocks.

After light emission is started under such conditions, the skin is rejuvenated in accordance with the wavelength and the intensity (irradiance and irradiation time) of light. Changes of the skin conditions as a result of the rejuvenation appear as the changes of the blood flow.

In Step S1200, the operation determining unit 320 selects one of blocks 540 that are being irradiated with light. The operation determining unit 320 handles a process up to a transition of operations after Step S1800, which is described below, as one processing cycle.

In Step S1300, all the skin-condition sensors in the selected block are caused to measure the blood flow again. The operation determining unit 320 calculates the block detection value from the newly obtained measurement values. If the block includes only one skin detection sensor, calculation of the mean value is not required. The operation determining unit 320 then calculates the difference between the initial block detection value and the newly calculated block detection value for the selected block (hereinafter the difference is referred to as a "detection difference").

In Step S1400, the operation determining unit 320 obtains the threshold parameter 554 corresponding to the selected block from the control rule table 550 (see FIG. 7). The operation determining unit 320 calculates the threshold of the detection difference on the basis of the initial block detection value and the threshold parameter 554 for the selected block.

For example, the threshold parameter 554 is assumed to be a value "40%", expressing the percentage of an increase of the blood flow with respect to the initial blood flow. In this case, the operation determining unit 320 calculates the threshold by multiplying the initial block detection value by "0.4", which is a value obtained by dividing the value of the threshold parameter 554 by 100.

The operation determining unit 320 then determines whether or not the detection difference calculated in Step S1300 has exceeded the calculated threshold (predetermined threshold). In the case where the detection difference has not exceeded the predetermined threshold (NO in S1400), the processing of the operation determining unit 320 proceeds to Step S1600. In the case where the detection difference has exceeded the predetermined threshold (YES in S1400), the processing of the operation determining unit 320 proceeds to Step S1500.

Here, the case where the detection difference has not arrived at the predetermined threshold is the state where the skin has not yet been fully rejuvenated by light irradiation. The case where the detection difference has arrived at the predetermined threshold is the state where the skin has been fully rejuvenated by light irradiation and before the light irradiation becomes excessive.

In Step S1500, the operation determining unit 320 stops or reduces light emission of the light-emitting device units in the selected block. At this time, desirably, the operation determining unit 320 gradually reduces the intensity of light from the light-emitting device units. This is for the purpose of preventing the blood-flow balance between adjacent blocks from being lost as a result of a sudden increase of the intensity difference between a block for which light emission is stopped or reduced and adjacent blocks to which light has been continuously emitted. The intensity of light is gradually reduced, for example, at such a pace as to be approximately halved per minute.

In Step S1600, the operation determining unit 320 determines whether or not there is any block that is being irradiated with light and that has not been selected in this cycle. In the case where there is any block that is being irradiated with light and that has not been selected (YES in S1600), the processing of the operation determining unit 320 proceeds to Step S1700. In the case where there is no block that is being irradiated with light and that has not been selected (NO in S1600), the processing of the operation determining unit 320 proceeds to Step S1800.

In Step S1700, the operation determining unit 320 selects one of the blocks 540 that is being irradiated with light and that have not been selected and returns to Step S1300.

In Step S1800, the operation determining unit 320 determines whether or not there is any block that is being irradiated with light. When there is any block that is being irradiated with light, (YES in S1800), the processing of the operation determining unit 320 returns to Step S1200. When there is no block that is being irradiated with light, (NO in S1800), the processing of the operation determining unit 320 is finished.

By performing these operations, the phototherapeutic device 100 is capable of periodically monitoring each block to see whether or not the skin has been fully rejuvenated by light irradiation and capable of stopping the light irradiation before the light irradiation becomes excessive.

Effects of Phototherapeutic Device

As described above, the phototherapeutic device 100 according to the embodiment is capable of emitting light having an appropriate intensity to each portion of the skin in accordance with the condition of the portion without users having to determine the intensity or irradiance of light that is to be applied to the portion.

Thus, the phototherapeutic device 100 according to the embodiment is capable of rejuvenating the skin of the entire face in balance while excessive light irradiation is prevented even when the skin conditions of the entire face is not uniform. In short, the phototherapeutic device 100 according to the embodiment is capable of effectively rejuvenating the skin.

The phototherapeutic device 100 according to the embodiment emits not only light of a color effective for rejuvenation of the skin but also light of a blue range that has an effect of sterilizing acne bacteria. Thus, the phototherapeutic device 100 is capable of further satisfying users, particularly the younger generation.

The phototherapeutic device 100 according to the embodiment is also capable of emitting light without the user holding the device with his/her hands. Thus, the user can use the phototherapeutic device 100 while performing other operations.

The phototherapeutic device 100 according to the embodiment is capable of saving power consumption to obtain the same irradiance since the distance from the light source to the skin is short, whereby the phototherapeutic device 100 can perform phototherapy in an environment-friendly manner.

The phototherapeutic device 100 according to the embodiment also emits light of the red range. Thus, the phototherapeutic device 100 is also effective in promoting the growth of, such as, eyebrows, eyelashes, hairline at the forehead, or beard. In the case where a sheet that covers other portions of the body besides the face, which will be described below, is used in the phototherapeutic device 100, the phototherapeutic device 100 can promote the growth of, for example, chest hair.

Modified Example of Phototherapeutic Device

The operation determining unit 320 may determine the type (color) of light and the initial irradiance of light with which each block is irradiated in accordance with the skin conditions.

In this case, the phototherapeutic device 100 is configured so that the operation determining unit 320 is capable of individually controlling the operation of the light-emitting devices of different colors. A table that describes the skin conditions and the operations that are to be performed by the different light-emitting devices in association with each other is stored in advance in the information storage unit 310. The skin condition sensors are sensors that are capable of detecting whether or not the corresponding portions are in the skin condition described in the table. On the basis of the detection results of each skin-condition sensor, the operation determining unit 320 determines the operation of the light-emitting devices with reference to the table.

For example, the discoloration of the skin can be detected by comparing the colors of different portions of the skin. Particularly, when detection is performed with emission of blue light, the discoloration formed at a deep portion of the skin can be accurately detected. The discoloration can be reduced by being irradiated with light of the yellow range.

Each skin-condition sensor may include a tone sensor to detect the tone of the skin. Examples usable as a tone sensor include a device that measures the intensity of light having wavelengths corresponding to colors of RGB using a photosensor or a device that can capture three primary colors of RGB using an organic semiconductor device described in "Trend in Research on Organic Imaging Devices" written by Satoshi AIHARA and Misao KUBOTA, in NHK Science & Technology Research Laboratories R&D No. 132, issued by NHK Science & Technology Research Laboratories, in March 2012, pp. 4 to 11. The tone sensor described in "Trend in Research on Organic Imaging Devices" written by Satoshi AIHARA and Misao KUBOTA, in NHK Science & Technology Research Laboratories R&D No. 132, issued by NHK Science & Technology Research Laboratories, in March 2012, pp. 4 to 11 can be finely fabricated by printing.

In this case, the operation determining unit 320 compares the detected tones of different portions of the skin and determines, block by block, whether or not each block has discoloration and how much degree the discoloration is. The operation determining unit 320 then determines the intensity of light of the yellow range for each block in accordance with the determined results. Specifically, the operation determining unit 320 increases the irradiance of light with which a block having heavy discoloration is irradiated by, for example, raising the predetermined threshold for the block having heavy discoloration compared to the threshold for other blocks to increase the irradiation time for the block having heavy discoloration.

When the light emission control is changed depending on the skin conditions, a table that describes, for example, the information indicating the skin conditions, the irradiance for each color range, the threshold corresponding to the upper limit of rejuvenation of the skin for each color range, and the maximum irradiation time for each color range in association with one another has to be stored in advance in the information storage unit 310.

In the case where each skin-condition sensor includes a tone sensor, the operation determining unit 320 may reduce or stop emission of light applied to each block when the degree of change of the skin color has arrived at a predetermined threshold. This is because the skin color represents the state of blood circulation (darkening) of the skin, that is, the degree of rejuvenation of the skin.

In the case where each skin-condition sensor includes a tone sensor, the tone sensor may detect the skin tone using light emitted from light sources other than the light-emitting device units. This is because the tone sensor is not used for image capturing and thus reflected light obtained when ambient light such as illumination from a dresser is incident on and reflected off the skin is bright enough for use in the spectroscopic analysis. In this case, the sheet member 210 needs to allow light to pass therethrough.

Desirably, the tone sensor is disposed on the sheet device 200 in such a manner as not to come into contact with the skin so that the toner sensor can capture light reflected off the skin.

Figure 9:
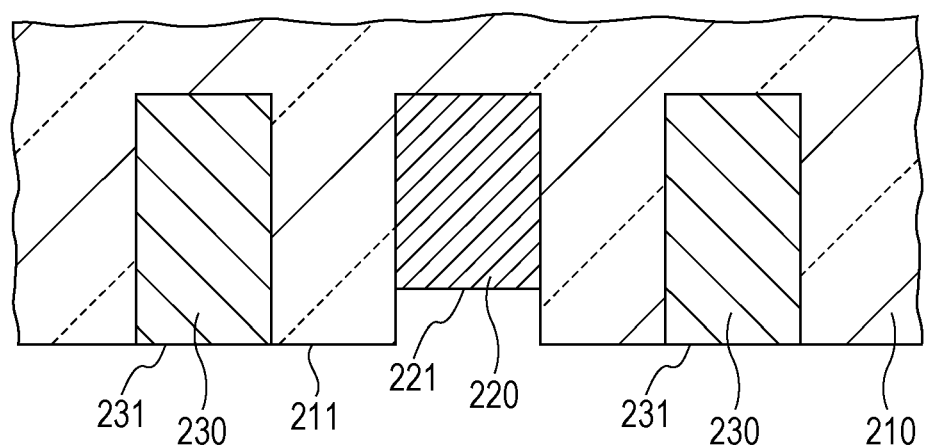
FIG. 9 illustrates an example of a cross section of the sheet device according to the second embodiment.

FIG. 9 illustrates an example of a cross section of the sheet device 200 including a tone sensor. FIG. 9 illustrates a portion of the entire sheet device 200.

As illustrated in FIG. 9, the light emission surface 231 of each light-emitting device 230 is positioned substantially flush with the surface 211 of the sheet member 210 that comes into close contact with the skin (the surface is hereinafter referred to as a "close contact surface"). On the other hand, the light receiving surface 221 of the skin-condition sensor 220 (tone sensor) is set back inward from the close contact surface 211 of the sheet member 210. For example, the light receiving surface 221 of the skin-condition sensor 220 is spaced apart from the skin by approximately 100 micrometers while the close contact surface 211 of the sheet member 210 is in close contact with the skin.

In the case where the skin-condition sensor 220 includes a tone sensor, the outputs from the light-emitting devices of different colors have to be balanced throughout the blocks so as to satisfy a predetermined balance. Thus, it is desirable that the operation determining unit 320 has a function of calibrating outputs from the light-emitting devices of different colors. The calibration is performed by, for example, adjusting outputs from the light-emitting devices so that the detection values from the tone sensor obtained when white paper is applied to the close contact surface 211 of the sheet member 210 approximate a predetermined value.

Besides the change of the blood flow or the skin color, the degree of rejuvenation of the skin is expressed in, for example, a change of the skin temperature. Thus, the phototherapeutic device 100 may include a temperature sensor as a skin-condition sensor and stop light emission in accordance with the change of the detected skin temperature. In this case, an example usable as a standard for determining a stop of light emission is an increase in temperature by one degree. It is desirable that the determination with respect to the temperature be made on the basis of the absolute values whereas the determination with respect to the blood flow be made on the basis of the relative values. An example usable as a temperature sensor is a temperature sensor in which an organic molecule layer of an organic thin film transistor is formed of a phthalocyanine nano-size structure (see, for example, International Publication No. 2013/151128).

The phototherapeutic device 100 may alternatively control light emission on the basis of both the change of blood flow and the change of the temperature. In this case, it is desirable that the phototherapeutic device 100 stop emission of light applied to eyelid portions when the degree of change of the temperature at the eyelid portions exceeds a predetermined threshold regardless of the degree of the change of blood flow to prevent the high temperature from imposing a load on the skin at the eyelid portions. The phototherapeutic device can have a high temperature due to a breakdown, whereby stopping light emission in response to such a temperature change also enhances the product safety.

At least one of the functions of the control unit 300 according to the second embodiment may be implemented by other devices having different functions, such as mobile phones.

At least one of the functions of the control unit 300 may be implemented by a network server. Specifically, at least one of the functions of the phototherapeutic device may be implemented by cloud computing. In this case, the operation determining unit needs to include at least a communication unit, transmit data of the skin conditions to the server, and obtain timing of stopping light emission.

A sheet that covers portions of the body other than the face is usable in the phototherapeutic device 100. In this case, for example, the use of the phototherapeutic device 100 can effectively reduce macular discoloration on the back due to a sunburn or other causes.

The phototherapeutic device 100 may have operation determining units 320 corresponding to different blocks, each of the operation determining units 320 performing operations for the corresponding block.

The phototherapeutic device of this disclosure includes a sheet member that is attachable to a skin; a skin-condition sensor that is disposed in the sheet member and that detects information related to a condition of the skin; and a light-emitting device unit that is disposed in the sheet member, the light-emitting device unit operating on the basis of the information detected by the skin-condition sensor, wherein the light-emitting device unit includes a plurality of light-emitting devices that emit light having different wavelengths.

In the phototherapeutic device, the light-emitting device unit may reduce or stop light emission when the degree to which the information detected by the skin-condition sensor changes arrives at a predetermined threshold after a start of the light emission.

In the phototherapeutic device, a plurality of skin-condition sensors may be disposed at different positions of the sheet member, each of the skin-condition sensors may detect information related to a condition of a portion of the skin, a plurality of light-emitting device units may be disposed at different positions of the sheet member, each of the light-emitting device units may be disposed at a position corresponding to at least one of the skin-condition sensors, each of the light-emitting device units may operate on the basis of the information detected by the at least one corresponding skin-condition sensor.

In the phototherapeutic device, the sheet member may be attached to a predetermined portion of a face, the light-emitting device unit may irradiate the skin with predetermined light that facilitates rejuvenation of the skin, the skin-condition sensor may detect at least one of a blood flow and a temperature of the skin as the information related to the condition, and the predetermined threshold may be determined for each of the light-emitting devices by using, as a reference, the condition of the skin before the information detected by the skin-condition sensor changes.

In the phototherapeutic device, the sheet member may include a first region corresponding to one eyelid portion of the face and a second region different from the first region, the plurality of light-emitting device units may include a second light-emitting device unit disposed in the first region and a third light-emitting device unit disposed in the second region, the second light-emitting device unit emits light having an intensity lower than an intensity of light emitted by the third light-emitting device unit, and a predetermined threshold for the second light-emitting device unit may be lower than a predetermined threshold for the third light-emitting device unit.

In the phototherapeutic device, each of the light-emitting device units may gradually reduce the intensity of light when stopping the light emission.

In the phototherapeutic, the sheet member may include a plurality of sections, at least one of the skin-condition sensors may be disposed in each of the sections, at least one of the light-emitting device units may be disposed in each of the sections, and the phototherapeutic device may include an operation determining unit that determines an operation of the at least one light-emitting device unit disposed in one section on the basis of information detected by the at least one skin-condition sensor disposed in said one section.

In the phototherapeutic device, the light-emitting device unit may include a blue light emitting device, the skin-condition sensor may detect a tone of the skin as the information related to the condition of the skin in a state where the blue light emitting device is emitting light, and the operation determining unit may determine an intensity of light that is to be emitted by the light-emitting device unit on the basis of the tone.

In the phototherapeutic device, the sheet member may be detachably connected to the operation determining unit using a connector and a cable.

A phototherapeutic method according to this disclosure include detecting information related to a condition of a skin using a skin-condition sensor disposed on a sheet member attachable to the skin; and operating a light-emitting device unit disposed in the sheet member on the basis of the information detected by the skin-condition sensor.

The disclosure is usable as a device such as a phototherapeutic device that can more effectively rejuvenate the skin.

What is claimed is:
1. A phototherapeutic device comprising:
 a face sheet that is attachable to a skin, the face sheet including a plurality of blocks including a first block corresponding to an eyelid portion of a face and a second block corresponding a non-eyelid portion of the face, the non-eyelid portion being different from eyelid portions of the face including the eyelid portion;
a first light-emitter that is disposed within the first block and emits first light;
a second light-emitter that is disposed within the second block and emits second light;
a first skin-condition sensor that is disposed within the first block and detects a first value before emission of the first light and a second value during emission of the first light, the first and second values relating to conditions of a skin of the eyelid portion;
a second skin-condition sensor that is disposed within the second block and detects a third value before emission of the second light and a fourth value during emission of the second light, the third and fourth values relating to conditions of a skin of the non-eyelid portion; and
a controller that
  causes the first skin-condition sensor and the second skin-condition sensor to detect the first value and the third value before emission of the first light and the second light by the first light-emitter and the second light-emitter, respectively;
  causes the first light-emitter and the second light-emitter to emit the first light with a first intensity and the second light with a second intensity, respectively, such that the first intensity is lower than the second intensity;
  selects a block of the plurality of blocks that is emitting light and performs a process for the selected block, the process for the selected block comprising:
  determining whether the selected block is the first block or the second block;
  when the selected block is determined to be the first block,
    causing the first skin-condition sensor to detect the second value during emission of the first light; and
    reducing or stopping the first light emitted by the first light-emitter when an absolute difference between the first value and the second value is greater than a first threshold,
  when the selected block is determined to be the second block,
    causing the second skin-condition sensor to detect the fourth value during emission of the second light; and
    reducing or stopping the second light emitted by the second light-emitter when an absolute difference between the third value and the fourth value is greater than a second threshold, the second threshold being greater than the first threshold,
the controller further determines whether a block emitting light is present after the process for the selected block is completed; and
when a block emitting light is present, the controller selects the block emitting light and repeats the process for the selected block, until the controller does not detect a block emitting light.

2. The phototherapeutic device according to claim 1, wherein, when the first block is adjacent to the second block, the controller reduces the second intensity of the second light emitted by the second light-emitter by half in a minute, when the absolute difference between the third value and the fourth value is greater than the second threshold and the absolute difference between the first value and the second value is equal to or smaller than the first threshold.

3. The phototherapeutic device according to claim 1, further comprising:
a first blue light emitter that is disposed within the first block,
wherein the first skin-condition sensor detects tones of the skin of the eyelid portion as the conditions of the skin of the eyelid portion when the first blue light emitter is emitting blue light, and
wherein a light receiving surface of the first skin-condition sensor is set back inward from a surface of the face sheet contacting the skin.

4. The phototherapeutic device according to claim 1, further comprising:
a third skin-condition sensor that is disposed in the first block and detects a first temperature before emission of the first light and a second temperature during emission of the first light,
wherein the first skin-condition sensor detects blood flows, as the conditions of the skin of the eyelid portion, and the second skin-condition sensor detects blood flows, as the conditions of the skin of the non-eyelid portion,
wherein the controller causes the first light-emitter to stop the first light when an absolute difference between the first temperature and the second temperature is greater than a third threshold and the absolute difference between the first value and the second value is equal to or smaller than the first threshold.

5. A phototherapeutic method, using a face sheet attachable to the skin and including a plurality of blocks including a first block corresponding to an eyelid portion of a face and a second block corresponding a non-eyelid portion of the face, the non-eyelid portion being different from eyelid portions of the face including the eyelid portion; a first light-emitter that is disposed within the first block and emits first light; a second light-emitter that is disposed within the second block and emits second light; a first skin-condition sensor that is disposed within the first block and detects a first value before emission of the first light and a second value during emission of the first light, the first and second values relating to conditions of a skin of the eyelid portion; and a second skin-condition sensor that is disposed within the second block and detects a third value before emission of the second light and a fourth value during emission of the second light, the third and fourth values relating to conditions of a skin of the non-eyelid portion,
the method comprising:
detecting, by the first skin-condition sensor and the second skin-condition sensor, the first value and the third value before emission of the first light and the second light by the first light-emitter and the second-light emitter, respectively; and
emitting, by the first light-emitter and the second light-emitter, the first light with a first intensity and the second light with a second intensity, respectively, such that the first intensity is lower than the second intensity;
selecting a block of the plurality of blocks that is emitting light and performing a process for the selected block, the process for the selected block comprising:
  determining whether the selected block is the first block or the second block;
  when the selected block is determined to be the first block,
    detecting, by the first skin-condition sensor, the second value during emission of the first light by the first light-emitter; and reducing or stopping the first light emitted by the first light-emitter when an absolute difference between the first value and the second value is greater than a first threshold, when the selected block is determined to be the second block, detecting, by the second skin-condition sensor, the fourth value during emission of the second light by the second light-emitter; and reducing or stopping the second light emitted by the second light-emitter when an absolute difference between the third value and the fourth value is greater than a second threshold, the second threshold being greater than the first threshold, determining whether a block emitting light is present after the process for the selected block is completed; and selecting, when a block emitting light is present, the block emitting light and repeating the process for the selected block, until a block emitting light is not detected.

6. A phototherapeutic device comprising:

a face sheet that is attachable to a skin, the face sheet including a first region corresponding to an eyelid portion of a face and a second region corresponding a non-eyelid portion of the face, the non-eyelid portion being different from eyelid portions of the face including the eyelid portion;

a first light-emitter that is disposed within the first region and emits first light;

a second light-emitter that is disposed within the second region and emits second light;

a first skin-condition sensor that is disposed within the first region and detects a first value before emission of the first light and a second value during emission of the first light, the first and second values relating to conditions of a skin of the eyelid portion;

a second skin-condition sensor that is disposed within the second region and detects a third value before emission of the second light and a fourth value during emission of the second light, the third and fourth values relating to conditions of a skin of the non-eyelid portion;

a storage that stores a first threshold parameter and a second threshold parameter in association with the first region and the second region, respectively, a controller that causes the first skin-condition sensor and the second skin-condition sensor to detect the first value and the third value before emission of the first light and the second light, respectively;

causes the first light-emitter and the second light-emitter to emit the first light with a first intensity and the second light with a second intensity, respectively, such that the first intensity is lower than the second intensity, determines a first threshold for the first skin-condition sensor, based on the first value detected by the first skin-condition sensor and the first threshold parameter stored in the storage, determines a second threshold for the second skin-condition sensor, based on the second value detected by the second skin-condition sensor and the second threshold parameter stored in the storage, the first threshold being lower than the second threshold, reduces or stops the first light emitted by the first light-emitter when an absolute difference between the first value and the second value is greater than the first threshold, and reduces or stops the second light emitted by the second light-emitter when an absolute difference between the third value and the fourth value is greater than the second threshold.

7. The phototherapeutic device according to claim 6, wherein, when the first region is adjacent to the second region, the controller reduces the second intensity of the second light emitted by the second light-emitter by half in a minute, when the absolute difference between the third value and the fourth value is greater than the second threshold and the absolute difference between the first value and the second value is equal to or smaller than the first threshold.

8. The phototherapeutic device according to claim 6, further comprising:

a first blue light emitter that is disposed within the first region, wherein the first skin-condition sensor detects tones of the skin of the eyelid portion as the conditions of the skin of the eyelid portion when the first blue light emitter is emitting blue light, and wherein a light receiving surface of the first skin-condition sensor is set back inward from a surface of the face sheet contacting the skin.

9. The phototherapeutic device according to claim 6, further comprising:

a third skin-condition sensor that is disposed in the first region and detects a first temperature before emission of the first light and a second temperature during emission of the first light, wherein the first skin-condition sensor detects blood flows, as the conditions of the skin of the eyelid portion, and the second skin-condition sensor detects blood flows, as the conditions of the skin of the non-eyelid portion, wherein the controller causes the first light-emitter to stop the first light when an absolute difference between the first temperature and the second temperature is greater than a third threshold and the absolute difference between the first value and the second value is equal to or smaller than the first threshold.

* * * * *